United States Patent
Zhang et al.

(10) Patent No.: US 8,224,445 B2
(45) Date of Patent: *Jul. 17, 2012

(54) FAR-FIELD SENSING CHANNEL FOR IMPLANTABLE CARDIAC DEVICE

(75) Inventors: Geng Zhang, Newbury Park, CA (US); Douglas R. Daum, Woodbury, MN (US); James O. Gilkerson, Stillwater, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,387

(22) Filed: Aug. 8, 2011

(65) Prior Publication Data

US 2011/0295136 A1    Dec. 1, 2011

Related U.S. Application Data

(63) Continuation of application No. 10/858,848, filed on Jun. 2, 2004, now Pat. No. 7,996,083.

(51) Int. Cl.
*A61N 1/37* (2006.01)
(52) U.S. Cl. .............................. 607/9; 607/28
(58) Field of Classification Search .................... 607/28, 607/9
See application file for complete search history.

(56) References Cited

U.S. PATENT DOCUMENTS

| | | | |
|---|---|---|---|
| 5,193,550 A | 3/1993 | Duffin |
| 5,331,966 A | 7/1994 | Bennett et al. |
| 5,404,877 A | 4/1995 | Nolan et al. |
| 5,411,031 A | 5/1995 | Yomtov |
| 5,417,717 A | 5/1995 | Salo et al. |
| 5,562,712 A | 10/1996 | Steinhaus et al. |
| 5,738,105 A | 4/1998 | Kroll |
| 5,987,352 A | 11/1999 | Klein et al. |
| 5,999,853 A | 12/1999 | Stoop et al. |
| 6,076,015 A | 6/2000 | Hartley et al. |
| 6,108,577 A | 8/2000 | Benser |
| 6,161,042 A | 12/2000 | Hartley et al. |
| 6,230,059 B1 | 5/2001 | Duffin |
| 6,236,882 B1 | 5/2001 | Lee et al. |
| 6,411,848 B2 | 6/2002 | Kramer et al. |
| 6,449,503 B1 | 9/2002 | Hsu |
| 6,496,715 B1 | 12/2002 | Lee et al. |
| 6,501,983 B1 | 12/2002 | Natarajan et al. |
| 6,539,257 B1 | 3/2003 | KenKnight |
| 6,539,259 B1 | 3/2003 | Weinberg et al. |
| 6,625,490 B1 | 9/2003 | McClure et al. |
| 6,699,200 B2 | 3/2004 | Cao et al. |
| 2002/0128688 A1 | 9/2002 | Stoop et al. |

(Continued)

OTHER PUBLICATIONS

"U.S. Appl. No. 10/858,848, Final Office Action mailed Dec. 11, 2008", 8 pgs.

(Continued)

*Primary Examiner* — Michael Kahelin
(74) *Attorney, Agent, or Firm* — Schwegman, Lundberg & Woessner, P.A.

(57) ABSTRACT

An implantable pacemaker is provided with a far-field sensing channel which requires a reduced refractory period during the time when pacing pulses are delivered as compared with sensing channels using intra-cardiac electrodes. The far-field sensing channel may use the conductive housing of the implantable device or can and an indifferent electrode mounted on the device header as the electrodes for its differential inputs. Such a far-field sensing channel is able to sense activity occurring in either the atria or the ventricles for the purposes of arrhythmia detection and/or capture verification.

20 Claims, 2 Drawing Sheets

U.S. PATENT DOCUMENTS

2005/0288719 A1    12/2005    Zhang et al.

OTHER PUBLICATIONS

"U.S. Appl. No. 10/858,848, Response filed Oct. 17, 2008 to Non Final Office Action mailed Jul. 17, 2008", 9 pgs.

"U.S. Appl. No. 10/858,848, Final Office Action mailed Dec. 5, 2007", 9 pgs.

"U.S. Appl. No. 10/858,848, Non-Final Office Action mailed Jul. 17, 2008", 10 pgs.

"U.S. Appl. No. 10/858,848, Response filed Oct. 9, 2007 to Office Action mailed May 7, 2007", 10 pgs.

"U.S. Appl. No. 10/858,848, Response filed Feb. 5, 2008 to Final Office Action mailed Dec. 5, 2007", 9 pgs.

"U.S. Appl. No. 10/858,848, Advisory Action mailed Feb. 13, 2008", 3 pgs.

"U.S. Appl. No. 10/858,848, Final Office Action mailed Jan. 4, 2010", 8 pgs.

"U.S. Appl. No. 10/858,848, Final Office Action mailed Nov. 5, 2010", 9 pgs.

"U.S. Appl. No. 10/858,848, Final Office Action mailed Dec. 5, 2007", 8 pgs.

"U.S. Appl. No. 10/858,848, Final Office Action mailed May 8, 2006", 8 pgs.

"U.S. Appl. No. 10/858,848, Non Final Office Action mailed May 7, 2007", 7 pgs.

"U.S. Appl. No. 10/858,848, Non Final Office Action mailed Sep. 30, 2005", 9 pgs.

"U.S. Appl. No. 10/858,848, Non-Final Office Action mailed Jun. 2, 2009", 9 pgs.

"U.S. Appl. No. 10/858,848, Non-Final Office Action mailed Jun. 18, 2010", 8 pgs.

"U.S. Appl. No. 10/858,848, Non-Final Office Action Response, mailed Oct. 2, 2009", 12 pgs.

"U.S. Appl. No. 10/858,848, Notice of Allowance mailed Mar. 30, 2011", 7 pgs.

"U.S. Appl. No. 10/858,848, Response filed Mar. 7, 2011 to Final Office Action mailed Nov. 5, 2010", 11 pgs.

"U.S. Appl. No. 10/858,848, Response filed Apr. 15, 2009 to Final Office Action mailed Dec. 11, 2008", 10 pgs.

"U.S. Appl. No. 10/858,848, Response filed May 3, 2010 to Final Office Action mailed Jan. 4, 2010", 10 pgs.

"U.S. Appl. No. 10/858,848, Response filed Sep. 17, 2010 to Non Final Office Action mailed Jun. 18, 2010", 11 pgs.

"U.S. Appl. No. 10/858,848, Response filed Oct. 2, 2009 to Non Final Office Action mailed Jun. 2, 2009", 12 pgs.

"U.S. Appl. No. 10/858,848, Response filed Feb. 28, 2006 to Non Final Office Action mailed Sep. 20, 2005", 9 pgs.

"U.S. Appl. No. 10/858,848, Response filed Sep. 8, 2006 to Final Office Action mailed May 8, 2006", 10 pgs.

FAR-FIELD SENSING CHANNEL FOR IMPLANTABLE CARDIAC DEVICE

CLAIM OF PRIORITY

This application is a continuation of and claims the benefit of priority under 35 U.S.C. §120 to U.S. patent application Ser. No. 10/858,848, filed on Jun. 2, 2004, now issued as U.S. Pat. No. 7,996,083, which is hereby incorporated by reference herein in its entirety.

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used in treatment of cardiac conduction disorders in order to improve the coordination of cardiac contractions, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities. Any device with a pacing functionality will be referred to herein simply as a pacemaker regardless of other functions it may be capable of performing.

Cardiac rhythm management devices such as described above monitor the electrical activity of the heart via one or more sensing channels so that pacing pulses or defibrillation shocks can be delivered appropriately. Such sensing channels usually include implanted leads which have electrodes disposed intravascularly near the heart, which leads may also be used for delivering pacing pulses or defibrillation shocks. The signals generated from such sensing channels are referred to as intra-cardiac electrograms and reflect the time course of depolarization and repolarization as the heart beats, similar to a surface electrocardiogram (ECG). A problem that arises when pacemakers use intra-cardiac electrogram signals to detect intrinsic activity, however, is that pacing pulses delivered by the pacemaker interfere with the electrogram signal. The usual method by which a pacemaker deals with this problem is to temporarily disable a sensing channel for a specified time interval when a pacing pulse is delivered, referred to as a refractory period. The refractory period typically includes a blanking interval, during which time the sense amplifiers are disabled to prevent their saturation by the pacing pulse, as well as additional time in order to avoid interpreting a pacing pulse or an after-potential as an intrinsic beat. The longer a sensing channel is rendered refractory, however, the more compromised is its ability to detect tachyarrhythmias. Long refractory periods also make it more difficult to utilize a sensing channel to detect the electrical activity of the heart resulting from a pacing pulse, referred to as an evoked response, in order to determine if the pacing pulse has captured the heart. The present disclosure relates to a means for improving this situation.

DETAILED DESCRIPTION

In order to deal with the problems described above, an implantable pacemaker may be provided with a far-field sensing channel which requires a reduced refractory period during the time when pacing pulses are delivered as compared with sensing channels using intra-cardiac electrodes. The far-field sensing channel may use the conductive housing of the implantable device or can and an indifferent electrode mounted on the device header as the electrodes for its differential inputs. In certain embodiments, the indifferent electrode may also be used as a current excitation electrode or voltage sensing electrode by a minute ventilation sensor. Such a far-field sensing channel is able to sense activity occurring in either the atria or the ventricles for the purposes of arrhythmia detection and/or capture verification. The morphology of the electrogram signal generated by the far-field sensing channel may also be analyzed for arrhythmia detection purposes such as detecting and/or distinguishing ventricular and supra-ventricular tachycardias. A description of an exemplary cardiac device which incorporates a far-field sensing channel is set forth below followed by a description of several different embodiments for using the far-field channel.

Figure 1:
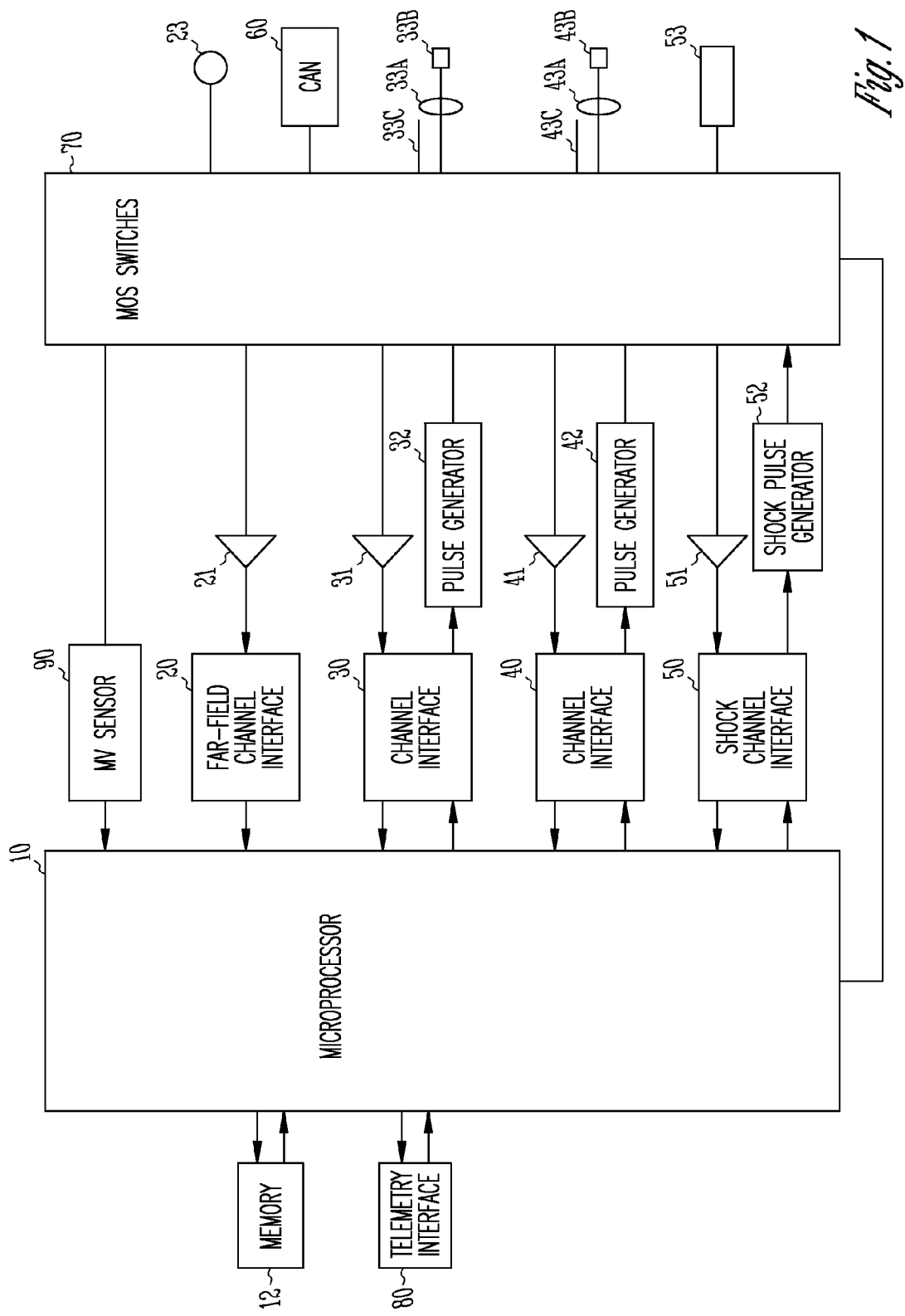
FIG. 1 is a functional block diagram of an implantable cardiac device.

Cardiac rhythm management devices are implantable devices that provide electrical stimulation to selected chambers of the heart in order to treat disorders of cardiac rhythm. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer or other device via a wireless telemetry link.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates atrial and ventricular senses when voltages sensed by the electrodes of a particular channel exceed a specified threshold. A ventricular sense would correspond to an R wave on an ECG, and an atrial sense would correspond to a P wave. The controller 10 interprets sense signals from the sensing channels in order to detect arrhythmias and to control the delivery of paces in accordance with a pacing algorithm that employs such senses to trigger or inhibit pacing. The electrogram signals can also be digitized and recorded (i.e., stored in memory) by the controller and then either transmitted via a telemetry link to an external programmer or maintained in memory or other storage medium for later transmission. The patient's cardiac activity may thus be observed in real-time or over a selected historical period.

The embodiment shown in FIG. 1 has two intra-cardiac sensing/pacing channels connected to the controller via a channel interface, where a pacing channel is made up of a pulse generator connected to an electrode while a sensing channel is made up of the sense amplifier connected to an electrode. The channel interfaces communicate bidirectionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70. In an example configuration, one intra-cardiac sensing/pacing channel includes ring electrode 43a and tip electrode 43b of bipolar lead 43c, sense amplifier 41, pulse generator 42, and a channel interface 40 while another intra-cardiac sensing/pacing channel includes ring electrode 33a and tip electrode 33b of bipolar lead 33c, sense amplifier 31, pulse generator 32, and a channel interface 30. The intra-cardiac channels may be configured as either atrial or ventricular channels. A dedicated far-field sensing channel is also shown made up of a channel interface 20, sense amplifier 21, and electrode 23 which can be disposed subcutaneously for generating a far-field electrogram. In certain devices, the far-field electrode 23 is mounted on the device housing. Also, more than one far-field electrode may be used in certain instances. The switch matrix may configure the sensing vector of the far-field channel by referencing the electrode 23 to the device housing or can or to other subcutaneous electrodes. A shock channel which includes a shock channel interface 50 and a shock pulse generator 52 is also provided for delivering defibrillation shocks between a shock electrode 53 and the housing or can 60 as selected by the switch matrix. The shock electrode is a coil electrode with a large surface area which can also be used to record an electrogram suitable for morphology analysis. The shock channel sensing vector may be configured with the coil referenced to the can or referenced to the can tied to another coil electrode. In the latter case, for example, proximal and distal coil electrodes may be incorporated into a shock lead with the sensing vector configured as the distal coil referenced to the can tied to the proximal electrode.

Also interfaced to the controller is a minute ventilation sensor 90 for use in measuring a parameter related to the patient's exertion level and adjusting the pacing rate of the device accordingly in rate-adaptive pacing modes. The minute ventilation sensor produces a signal which approximates the patient's exertion level by measuring respiratory volume rate. The minute ventilation sensor measures the respiratory volume by injecting bursts of excitation current between excitation electrodes and measuring a transthoracic voltage drop to derive a signal proportional to the transthoracic impedance. A particular minute ventilation sensor is described in U.S. Pat. No. 6,161,042, assigned to Cardiac Pacemakers, Inc. and hereby incorporated by reference in its entirety. The minute ventilation sensor comprises an exciter for supplying an oscillating excitation current between a pair of excitation current electrodes located in the patient's thoracic cavity and a pair of voltage sense electrodes for generating an impedance signal corresponding to a potential difference between two points in the thoracic cavity when the excitation current is applied. In one particular embodiment, the indifferent electrode 23 is utilized by the minute ventilation sensor as an excitation current electrode or a voltage sense electrode in addition to its use in the far-field sensing channel. In that case, the switch matrix may be operated so that the far-field sensing channel is active only during periods when no excitation current is being supplied.

Figure 2:
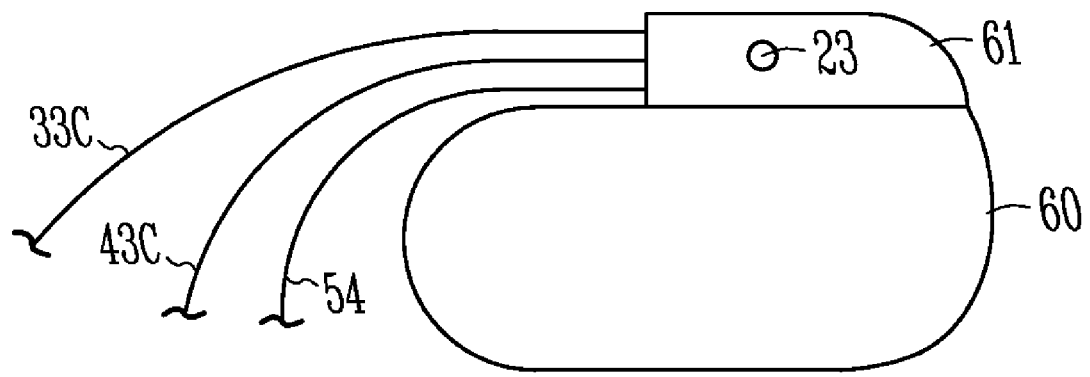
FIG. 2 shows the physical structure of an implantable cardiac device.

FIG. 2 is a physical depiction of the exemplary device described above with reference to FIG. 1. The device housing or can 60 is metallic and contains the therapy circuitry illustrated in FIG. 1. The therapy leads 33c, 43c, and 54 are connected to the therapy circuitry contained within the housing by means of a header 61 with feedthroughs located therein for routing the therapy leads to the appropriate internal components. Also shown is the indifferent electrode 23. Because the device header is made of insulating material, the indifferent electrode 23 may be mounted on the device header 61 and referenced to the can 60 to provide a far-field sensing vector.

As noted above, arrhythmias may be detected by measuring the intervals between sense signals in a heart chamber and employing a rate criterion to determine if an arrhythmia is present. When a sensing channel is blanked due to pacing, however, sense signals from a heart chamber may be missed which interferes with arrhythmia detection. Because the electrodes of the far-field sensing channel (i.e., the can and the indifferent electrode) are not involved in pacing when bipolar pacing is employed, the effect of pacing in this channel is just a very brief spike (a common mode shift). This means that the blanking interval necessary for the far-field channel may be made very brief, on the order of 1-2 ms as compared with the 15-20 ms blanking interval typically used for intra-cardiac sensing channels. The far-field sensing channel can therefore be left active for longer periods of time than can an intra-cardiac sensing channel. This can be exploited in one embodiment to more sensitively detect ventricular arrhythmias by configuring the controller or other circuitry to detect ventricular sense signals when the far-field electrogram signal amplitude exceeds a specified threshold value. Since R waves generated by the ventricles are much larger than the P waves generated by the atria, the threshold value can be set high enough so that only ventricular electrical activity produces a sense signal. The device then measures the intervals between the far-field sense signals to determine if a ventricular arrhythmia is present.

Detection of arrhythmias in either the atria or ventricles can also be affected by noise in the sensing channels which may cause oversensing. In oversensing, a sense is detected in a sensing channel when no contraction in the heart chamber has occurred. In order to lessen the probability of an arrhythmia being falsely detected, the far-field sensing channel may be employed to verify or cross-check senses detected in either an atrial and/or ventricular intra-cardiac sensing channel so that the sense signals are more specifically detected. In one embodiment, the capability of the far-field sensing channel to sense activity in both the atria and ventricles allows the cross-checking to be performed for both atrial and ventricular channels. If a sense is detected in an atrial or ventricular intra-cardiac channel, the sense is confirmed before being deemed as a true sense by determining whether a sense is simultaneously detected in the far-field channel. A sense is detected in the far-field channel if the electrogram signal amplitude exceeds a specified threshold and can be regarded as either an atrial or ventricular or sense in accordance with which intra-cardiac channel the sense being verified occurred. As noted above, ventricular R waves are larger in amplitude than atrial P waves so the thresholds for detecting atrial and ventricular senses in the far-field channel may be different.

Besides using a rate criterion for sense signals, another way of detecting arrhythmias is by analyzing the morphology of electrograms. The electrogram produced by the far-field sensing channel is similar in its morphology to that of a conventional surface ECG and reflects activity in both the atria and the ventricles. It is therefore especially suitable for use in morphology analysis by the controller of the implantable device or by an external device when the far-field electrogram is transmitted via the telemetry link. Morphology analysis of an electrogram waveform may involve cross-correlating the waveform with a template in order to determine if the waveform indicates an abnormal depolarization pattern. This type of analysis may be useful in detecting certain types of arrhythmias. Because the shock channel sensing "sees" a large volume of the myocardium, changes in the depolarization pattern of the heart will be more readily reflected in an electrogram generated by such a vector than in an intra-cardiac electrogram. Morphology analysis may be used, for example, in distinguishing ventricular tachycardias from supra-ventricular tachycardias as described in U.S. Pat. No. 6,449,503, assigned to Cardiac Pacemakers, Inc., the disclosure of which is hereby incorporated by reference in its entirety. The far-field sensing channel as described herein may be used in place of the shock channel for morphology analysis purposes or, in another embodiment, used to verify or cross-check the morphology analysis of the shock channel.

Another use for the far-field sensing channel is in capture verification. In order for a pacing pulse to have any effect on the heart, it must be of sufficient energy to cause a propagating wave of depolarization in the myocardium, termed an evoked response. If an evoked response occurs in a heart chamber as a result of a pacing pulse, the pacing pulse is said to have captured that heart chamber. It is useful for a pacemaker to determine if its pacing pulses are capturing the heart so that the pulse energy can be adjusted as needed by changing the duration and/or amplitude of the pacing pulse or a lead placement problem can be corrected. Automatic adjustment of pacing pulse energy by an implantable device is sometimes referred to as autocapture. Capture verification may be performed by detecting whether an evoked response occurs in a sensing channel for a particular heart chamber after a pacing pulse is delivered to that chamber. Once an atrial or ventricular pacing pulse is delivered, the device determines whether an electrogram signal in a sensing channel exceeds a specified threshold during a time window following the pace which indicates that an evoked response has occurred. The time window for determining whether an evoked response has occurred, however, is superceded by any blanking interval in the sensing channel following the pace. The aforementioned reduced blanking interval needed for the far-field sensing channel renders this channel especially suitable for capture verification as compared with intra-cardiac sensing channels. In a particular embodiment, after a pacing pulse is delivered to either an atrium or ventricle and after the short 1-2 ms blanking interval, the device compares the amplitude of the electrogram signal in the far-field sensing channel with a specified threshold value. Capture of the heart by the pacing pulse is then verified if the threshold value is exceeded by the far-field electrogram signal. The shorter blanking interval of the far-field sensing channel as compared with conventional intra-cardiac sensing channels reduces the chance that an evoked response will occur but fail to be detected.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A device comprising:
    sensing amplifiers for incorporating into atrial and ventricular sensing channels with intracardiac electrodes disposed near an atrium and ventricle, respectively;
    a pulse generator for incorporating into a pacing channel for delivering pacing pulses to a heart chamber;
    a sensing amplifier for incorporating into a far-field sensing channel having at least two far-field electrodes disposed in order to generate a far-field electrogram that reflects activity in both the atria and ventricles;
    a controller interfaced to the pacing and sensing channels and programmed with instructions for:
    upon delivery of a pacing pulse, disabling the atrial and ventricular sensing channels for a blanking interval on the order of 15-20 ms and disabling the far-field sensing channel for a blanking interval on the order of 1-2 ms; and,
    verifying capture of the heart chamber by the pacing pulse by determining whether an electrogram signal in the far-field sensing channel exceeds a specified threshold during a time window following the pacing pulse.

2. The device of claim 1 wherein the pulse generator is incorporated into a ventricular pacing channel.

3. The device of claim 1 wherein the pulse generator is incorporated into an atrial pacing channel.

4. The device of claim 1 further comprising:
    a minute ventilation sensor for measuring transthoracic impedance in order to generate a signal proportional to minute ventilation, the minute ventilation sensor including an exciter for supplying an oscillating excitation current between a pair of excitation current electrodes and a pair of voltage sense electrodes for generating an impedance signal;
    wherein one of the voltage sense electrodes is incorporated into the far-field sensing channel; and, wherein the controller is programmed such that the far-field sensing channel is made active only during periods when no excitation current is being supplied.

5. The device of claim 1 further comprising:
an implantable housing;
a header formed of insulating material mounted on the housing for receiving one or more sensing or pacing leads; and,
an indifferent electrode mounted on the header that serves as a far-field electrode.

6. The device of claim 1 further comprising:
an implantable conductive housing that serves as a far-field electrode;
a header formed of insulating material mounted on the housing for receiving one or more sensing or pacing leads; and,
an indifferent electrode mounted on the header that serves as a far-field electrode.

7. The device of claim 1 further comprising a subcutaneous electrode that serves as a far-held electrode.

8. The device of claim 1 further comprising:
an implantable conductive housing that serves as a far-field electrode; and,
a subcutaneous electrode that serves as a far-field electrode.

9. The device of claim 1 wherein the controller is further programmed with instructions for:
detecting a P-wave if two conditions are simultaneously met: 1) the atrial electrogram exceeds a specified atrial channel threshold, and 2) the far-field electrogram exceeds a specified far-field atrial threshold;
detecting an R-wave if two conditions are simultaneously met: 1) the ventricular electrogram exceeds a specified ventricular channel threshold, and 2) the far-field electrogram exceeds a specified far-field ventricular threshold;
wherein the far-field ventricular threshold is higher than the far-field atrial threshold; and,
detecting an arrhythmia when the intervals between detected P-waves or between detected R-waves meets a specified rate criterion.

10. The device of claim 9 further comprising:
a minute ventilation sensor for measuring transthoracic impedance in order to generate a signal proportional to minute ventilation, the minute ventilation sensor including an exciter for supplying an oscillating excitation current between a pair of excitation current electrodes and a pair of voltage sense electrodes for generating an impedance signal;
wherein one of the excitation current electrodes is incorporated into the far-field sensing channel; and,
wherein the controller is programmed such that the far-field sensing channel is made active only during periods when no excitation current is being supplied.

11. A method for operating a cardiac device comprising:
sensing atrial and ventricular activity via atrial and ventricular sensing channels having intracardiac electrodes disposed near an atrium and ventricle, respectively;
delivering pacing pulses to a heart chamber;
generating a far-field electrogram using a far-field sensing channel having at least two far-field electrodes disposed in order to reflect activity in both the atria and ventricles;
upon delivery of a pacing pulse, disabling the atrial and ventricular sensing channels for a blanking interval on the order of 15-20 ms and disabling the far-field sensing channel for a blanking interval on the order of 1-2 ms; and,
verifying capture of the heart chamber by the pacing pulse by determining whether an electrogram signal in the far-field sensing channel exceeds a specified threshold during a time window following the pacing pulse.

12. The method of claim 11 wherein the heart chamber to which pacing pulses are delivered by the pacing channel is a ventricle.

13. The method of claim 11 wherein the heart chamber to which pacing pulses are delivered by the pacing channel is an atrium.

14. The method of claim 11 further comprising:
measuring transthoracic impedance in order to generate a signal proportional to minute ventilation using a minute ventilation sensor, the minute ventilation sensor including an exciter for supplying an oscillating excitation current between a pair of excitation current electrodes and a pair of voltage sense electrodes for generating an impedance signal, wherein one of the voltage sense electrodes is incorporated into the far-field sensing channel; and,
making the far-field sensing channel active only during periods when no excitation current is being supplied.

15. The method of claim 11 further comprising employing an indifferent electrode mounted on a header of a device housing as a far-field electrode.

16. The method of claim 11 further comprising employing an implantable conductive device housing as a far-field electrode.

17. The method of claim 11 further comprising employing a subcutaneous electrode as a far-field electrode.

18. The method of claim 11 further comprising employing an implantable conductive housing and a subcutaneous electrode as a far-field electrodes.

19. The method of claim 11 further comprising:
detecting a P-wave if two conditions are simultaneously met: 1) the atrial electrogram exceeds a specified atrial channel threshold, and 2) the far-field electrogram exceeds a specified far-field atrial threshold;
detecting an R-wave if two conditions are simultaneously met: 1) the ventricular electrogram exceeds a specified ventricular channel threshold, and 2) the far-field electrogram exceeds a specified far-field ventricular threshold;
wherein the far-field ventricular threshold is higher than the far-field atrial threshold; and,
detecting an arrhythmia when the intervals between detected P-waves or between detected R-waves meets a specified rate criterion.

20. The method of claim 19 further comprising:
measuring transthoracic impedance in order to generate a signal proportional to minute ventilation using a minute ventilation sensor, the minute ventilation sensor including an exciter for supplying an oscillating excitation current between a pair of excitation current electrodes and a pair of voltage sense electrodes for generating an impedance signal, wherein one of the excitation current electrodes is incorporated into the far-field sensing channel; and,
making the far-field sensing channel active only during periods when no excitation current is being supplied.

* * * * *